United States Patent
Anderson et al.

(10) Patent No.: US 9,616,244 B2
(45) Date of Patent: Apr. 11, 2017

(54) EXTERNAL DEFIBRILLATOR

(75) Inventors: John McCune Anderson, Holywood (GB); Cesar Oswaldo Navarro-Paredes, Newtownabbey (GB); Rebecca DiMaio, Belfast (GB)

(73) Assignee: Heartsine Technologies Limited, Belfast (GB)

( * ) Notice: Subject to any disclaimer, the term of this patent is extended or adjusted under 35 U.S.C. 154(b) by 1077 days.

(21) Appl. No.: 13/318,162

(22) PCT Filed: Apr. 28, 2010

(86) PCT No.: PCT/EP2010/055742
§ 371 (c)(1),
(2), (4) Date: Oct. 31, 2011

(87) PCT Pub. No.: WO2010/125116
PCT Pub. Date: Nov. 4, 2010

(65) Prior Publication Data
US 2012/0046706 A1  Feb. 23, 2012

(30) Foreign Application Priority Data
May 1, 2009 (IE) .................... S2009/0348

(51) Int. Cl.
| A61N 1/00 | (2006.01) |
| A61N 1/39 | (2006.01) |
| A61B 5/046 | (2006.01) |
| G06K 9/00 | (2006.01) |
| A61B 5/04 | (2006.01) |

(52) U.S. Cl.
CPC ............ *A61N 1/3925* (2013.01); *A61B 5/046* (2013.01); *A61B 5/04012* (2013.01); *G06K 9/0053* (2013.01)

(58) Field of Classification Search
USPC .......................................... 607/5
See application file for complete search history.

(56) References Cited

U.S. PATENT DOCUMENTS

| 2004/0220489 A1 | 11/2004 | Sherman et al. |
| 2005/0245973 A1 | 11/2005 | Sherman |
| 2005/0245974 A1 | 11/2005 | Sherman |
| 2005/0256415 A1* | 11/2005 | Tan ...................... A61B 5/0464 600/509 |

(Continued)

OTHER PUBLICATIONS

Neurauter, et al., "Estimation of the duration of ventricular fibrillation using ECG single feature analysis", Resuscitation, Apr. 17, 2007, vol. 73, p. 246-252, Elsevier, IE.

(Continued)

Primary Examiner — Amanda Patton
Assistant Examiner — Philip C Edwards

(57) ABSTRACT

An external defibrillator estimates the phase of ventricular defibrillation (VF) by deriving, from an ECG exhibiting VF, at least one quality marker representing the morphology of the ECG and, therefore, the duration of the VF. The duration of the VF is calculated as a function of the value (s) of the quality marker (s). The quality marker (s) may comprise any one or more of the median slope of the ECG, the average slope of the ECG, the ratio of the power in relatively high and low frequency bands of the ECG, and a measure of the density and amplitude of peaks in the ECG, over a predetermined period.

11 Claims, 3 Drawing Sheets

(56) References Cited

U.S. PATENT DOCUMENTS

2008/0269818 A1   10/2008   Sullivan et al.

OTHER PUBLICATIONS

Zhu, et al., "Detection of ventricular fibrillation by sequential testing", Proceedings of Comp. in Cardiology Meeting, Sep. 25, 1988, p. 325-328, IEEE Comp. Soc. Press, US.
Brown et al., "Signal analysis of the human electrocardiogram . . . ", Annals of Emergency Medicine, vol. 27, No. 2, Feb. 1, 1996, p. 184-188, Amer. Col. of Emerg. Phys., US.

* cited by examiner

EXTERNAL DEFIBRILLATOR

FIELD OF THE INVENTION

This invention relates to an external defibrillator.

BACKGROUND

Following the publication of a three-phase time sensitive model by Weisfeldt and Becker (Weisfeldt M L, Becker L B: "Resuscitation after cardiac arrest. A 3-phase time-sensitive model"; JAMA. 2002; 288: 3035-3038), much research has focused on developing treatment algorithms specific to each of three phases of cardiac arrest.

The first phase is known as the "Electrical Phase" and constitutes the first four minutes of a cardiac arrest. During this time, immediate defibrillation should be administered.

The second phase is known as the "Circulatory Phase" and occurs after the first phase for another period of four minutes—that is, four to ten minutes after arrest. During this phase, CPR should be administered before defibrillation in order to increase perfusion and prepare the myocardium for defibrillation by re-oxygenation, thereby increasing the chances of success of the therapy.

The final phase is known as the "Metabolic Phase" and the only available treatments are mild or moderate hypothermia, metabolic therapies or the use of Caspase inhibitors, all of which are only applicable to in-hospital patients.

Studies have shown that survival rates are much lower for patients presenting prolonged ventricular fibrillation (VF). In these cases, immediate defibrillation appears to simply convert the patient's electrocardiogram (ECG) from one non-perfusing rhythm (i.e. VF) to another (i.e. PEA/asystole). It has also been shown that immediate defibrillation in cases of prolonged cardiac arrest would result from countershock-induced injury to ischemic myocardium.

The condition of the myocardium deteriorates rapidly without effective CPR to perfuse the heart muscle and other vital organs. It is widely accepted that, for VF of short duration (less than 4 mins since VF onset), immediate shock therapy is indicated, whereas for VF of long duration (more than 4 mins since VF onset), CPR prior to defibrillation increases the chances of return of spontaneous circulation (ROSC).

It is evident that if the responder had accurate information as to which phase of VF the patient was presenting, they could deliver the most appropriate form of therapy and improve their chances of survival.

SUMMARY OF THE INVENTION

According to the present invention there is provided an external defibrillator comprising means for estimating the phase of ventricular fibrillation (VF) by analysis of the patient's ECG and means dependent on the estimated phase for indicating whether an immediate shock or CPR is advised.

In certain embodiments the means for estimating the phase of VF comprises estimating VF duration and comparing the estimated duration with a threshold level. In such a case VF duration is preferably estimated by deriving at least one VF quality marker from a patient's ECG and calculating the duration of VF as a function of the value(s) of the quality marker(s).

The quality marker may comprise the median slope of the ECG over a predetermined period, the average slope of the ECG over a predetermined period, the ratio of the power in relatively high and low frequency bands of the ECG over a predetermined period, or a measure of the density and amplitude of peaks in the ECG over a predetermined period.

In another embodiment the means for estimating the phase of VF comprises deriving a quantity related to the density and amplitude of peaks in the ECG over a predetermined period.

In such case said quantity is derived by constructing an envelope of the ECG and measuring the average magnitude of peaks lying above the envelope during the predetermined period. The said quantity is preferably compared to a threshold level to estimate the phase of VF.

DESCRIPTION OF EMBODIMENTS OF THE INVENTION

Figure 1:
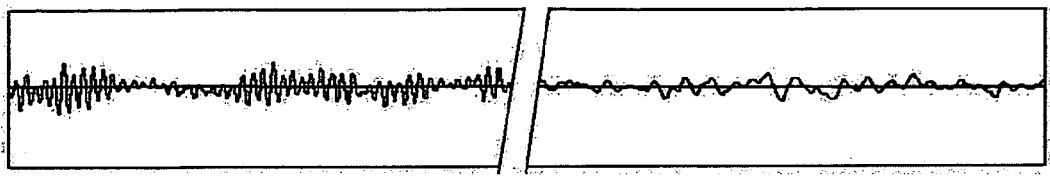
FIG. 1 shows how VF changes its morphology from its onset with time.

FIG. 1 shows how VF changes its morphology over time from its onset. An ECG exhibiting VF is shown in its early stages shortly after onset (left) and after 12 minutes (right). It can be seen that at the beginning of VF higher frequencies, higher amplitudes, higher slopes and a greater concentration of peaks are found. These changes in VF morphology reflect the worsening condition of the myocardium over time during uninterrupted VF.

The embodiments of the invention are based on the use of so-called "quality markers" for VF. In the present context a VF quality marker is a parameter, derived from an ECG exhibiting VF, which represents the morphology of the ECG and, therefore, it changes with the duration of the VF.

The embodiments teach a system incorporated into an automated external defibrillator (AED) which measures the ECG of a patient using the two defibrillator electrodes, calculates one or more VF quality markers and estimates, using an algorithm, the duration of the VF using the quality marker(s).

The prior art teaches two VF quality markers, referred to herein as Frequency Ratio (FR) and Median Slope (MS). In addition, two new VF quality markers are disclosed in the present specification, referred to herein as Density and Amplitude of Peaks (DA) and Average of Slopes (AS).

All, any or some of these quality markers can be used, in conjunction with the defibrillator's own diagnostic algorithm, to produce audible and visible indications to the operator to perform CPR prior the delivery of the shock in order to increase the chances of a successful resuscitation.

The VF Quality Markers

A sequence of ECG samples $x_0, x_1, \ldots, x_{N-1}$ in a window of N samples at fs samples per second is processed in successive epochs in order to obtain the following quality markers: Median Slope (MS), Average Slope (AS), Frequency Ratio (FR) and Density and Amplitude of Peaks (DA).

The Median Slope

The median slope as a shock outcome predictor is disclosed by Eilevstjonn et. al. (Eilevstjonn J, Kramer-Johansen J, Sunde K: "Shock outcome is related to prior rhythm and duration of ventricular fibrillation"; Resuscitation. 2007; 75 60-67).

The median slope (MS) is given by:

$$MS = \underset{i=1,2,\ldots,N-1}{\text{median}} \{(|x_i - x_{i-1}|)fs\}$$

For simplicity, the slope here is denoted by $x_i-x_{i-1}$ where two consecutive samples are used. However, many more points can be used for calculating the slope. The slopes are scaled and then sorted for the calculation of the median slope. By definition, the median is the central value of an array of N reordered samples. If N is odd, the value corresponding to the position (N+1)/2 in the array is the median. Otherwise (if N is even) the median is given by the semi-sum of the values in the array corresponding to the positions N/2 and N/2+1.

The Average Slope

The average slope (AS) is expressed by:

$$AS = \frac{1}{N-1} \sum_{i=1}^{N-1} (|x_i - x_{i-1}|)fs$$

The Frequency Ratio

The Frequency Ratio (FR) as an indicator of VF duration is disclosed by Sherman (Sherman L D: "The frequency ratio: An improved method to estimate ventricular fibrillation duration based on Fourier analysis of the waveform"; Resuscitation. 2006; 69: 479-486).

Sherman presented a method based on the frequency analysis of the VF waveform. VF data was recorded for 12.5 minutes in 45 swine. The Fourier frequency spectra were calculated for 5 second epochs. The average power at each frequency showed a marked loss of frequencies above 8 Hz occurring at 5 min accompanied by an increase in the power in frequency spectra from 3 to 5 Hz. The Frequency Ratio was defined as the ratio of the power in the high frequency band from 8 to 24 Hz compared to the power in the low frequency band from 3 to 5 Hz. The Frequency Ratio was shown to detect 90% of epochs in VF less than 5 min while allowing selection of 74% of those epochs over 5 min. When the Frequency Ratio was set to detect 90% of episodes of VF under 7 min, it was able to select 88% of those traces with VF over 7 min. The receiver operating curve (ROC) for the frequency ratio had an area under the curve of 0.91 at 5 min and 0.95 at 7 min of VF duration.

Sherman claims that the Frequency Ratio is a strong estimator of VF duration. However it is based on frequency analysis which is computationally costly especially for the proposed range of frequencies.

According to the procedure presented by Sherman, the sequence of samples $x_0, \ldots, x_{N-1}$ (in the time domain) is transformed into the sequence of N complex numbers $X_0, \ldots, X_{N-1}$ (in the frequency domain) by the Discrete Fourier Transform (DFT) according to the formula:

$$X_k = \sum_{n=0}^{N-1} x_n e^{-\frac{2\pi i}{N}kn} \quad k=0,1,\ldots,N-1$$

k=0, 1, . . . , N-1 where $$e^{\frac{2\pi i}{N}kn}$$

is a primitive $N^{th}$ root of unity.

Let $P_k = X_k \overline{X}_k$ the power at the frequency index k.

The low frequency band (3-5 Hz) is associated with the frequency indexes from $l_1$ to $l_n$.

Then the power of the low frequency band is found by:

$$P_{low} = \sum_{k=l_1}^{l_n} P_k$$

Similarly, the power of the high frequency band is given by:

$$P_{high} = \sum_{k=h_1}^{h_m} P_k$$

where $h_1$ and $h_m$ are the frequency indexes for the high frequency band (8-24 Hz).

Finally the Frequency Ratio (FR) is defined as:

$$FR = \frac{P_{high}}{P_{low}}$$

However, due to the fact that Fast Fourier Transforms (FFTs) are time consuming and use significant resources of the CPU, in the present embodiment the estimation of the magnitudes for different frequencies is carried out using integer filters—rather than analyse for all frequencies, filter through those, at discrete known frequencies, which are known to make the most significant contribution. This technique is described in our Irish Patent Application No. S2008/0785.

The Density and Amplitude of Peaks

For this quality marker an envelope of the ECG signal is used. At every sample it is checked if a peak is detected which is defined as an outstanding value outside the envelope. The envelope is an artificial and auto adjusted signal created from the ECG signal in order to contain it. However, an arriving sample, an outstanding one, can lie outside the envelope. The principle in deriving the envelope is to construct a ray aiming at the baseline at a particular rate but the ray can be reset by a sample "obstructing" its path to the baseline.

Figure 2:
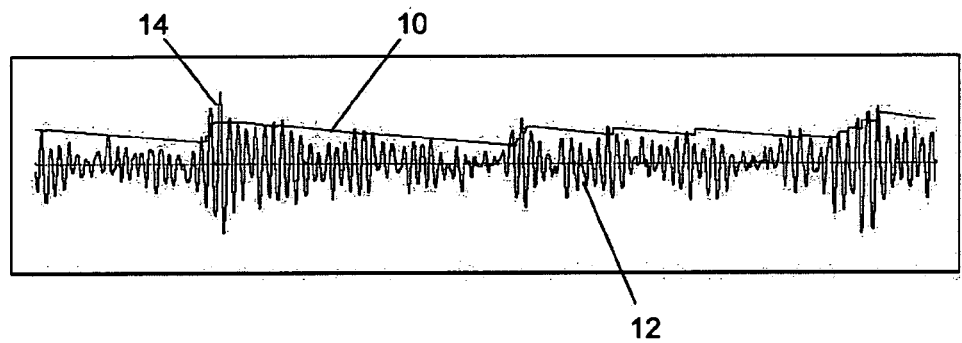
FIG. 2 shows the construction of an ECG envelope in one embodiment of the invention.

FIG. 2 is an example of an envelope for an ECG signal during VF. The envelope 10 "contains" the signal 12 providing an estimation of the maximum value of the signal at a particular instant. This (local) maximum value or peak aims at the baseline and is reset as the amplitude of the signal increases. As mentioned, certain peaks 14 may lie outside (i.e. above) the envelope.

Figure 3:
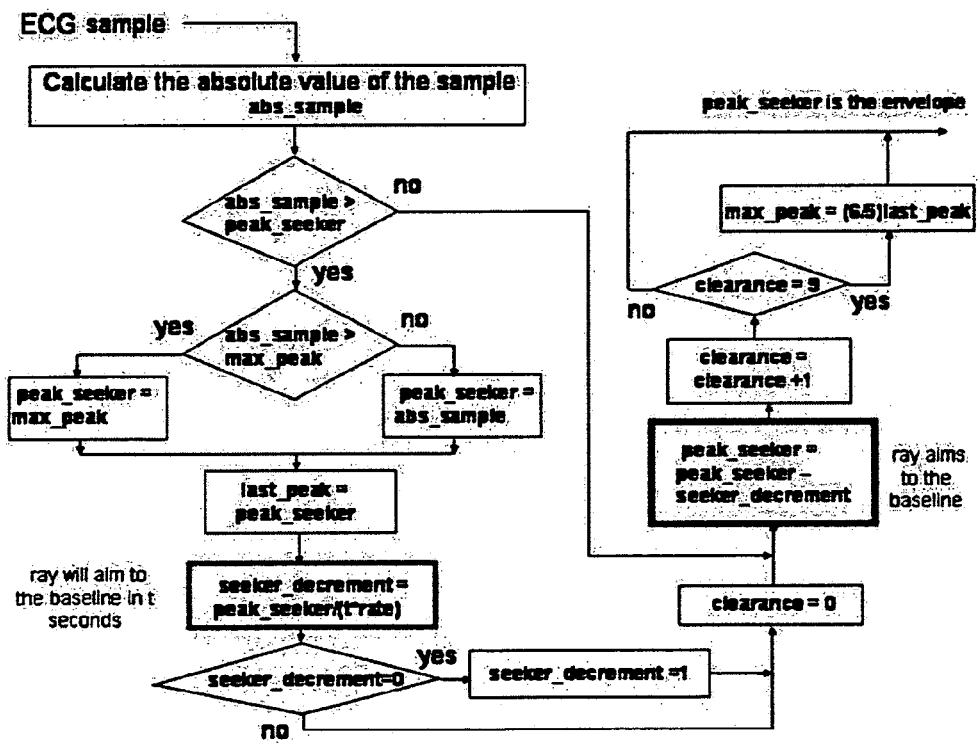
FIG. 3 is the flow diagram of an algorithm to calculate the envelope of FIG. 2 for use in an embodiment of the invention.

In FIG. 3 the flow diagram for the calculation of the envelope corresponding to each sample is presented. An explanation of the variables used and their initial values in digital units is presented in the following table:

| Variable | Description | Initial value |
| --- | --- | --- |
| sample: | ECG sample that feeds the algorithm at a rate of 170.6 samples/s | 0 |
| abs_sample: | Absolute value of sample. | 0 |
| envelope: | Artificially created signal that acts as a ray aiming to the baseline. In its path to the baseline it can be interrupted by an outstanding sample that reset its height. | 5000 uV |
| max_peak: | Propective value that potentially "climb" to an expected maximum. | 5000 uV |

-continued

| Variable | Description | Initial value |
|---|---|---|
| last_peak: | Keeps a record of the value outside the envelope encountered. | 5000 uV |
| seeker_decrement: | Value taken from the peak_seeker to give the following value for the peak_seeker. | 8 uV |
| clearance: | Counter to control when max_peak can be updated. | 0 |
| rate | Sample rate (samples per second) | 170.6 |

The parameters used in FIG. 2 and in the table above were used with a sample rate of 170.6 samples per second. However the parameters may change according to changes in the sample rate.

The Density of Peaks quality marker is given by:

$$DA = \frac{1}{N}\sum_{i=0}^{N-1} w_i$$

where: $w_i = x_i$ if $x_i$ is a peak lying outside (i.e. above) the envelope, otherwise $w_i = 0$.

If desired, the formula for DA can be multiplied by fs (the sample rate), as was done for the AS and MS quality markers. As fs is a constant, the effect of this multiplication will be just scaling but the original concept remains unchanged.

VF Duration

In order to compute an estimate of the VF duration from these markers, the following model is used:

$$t = -B + C\left[-\ln\left(\frac{Q-D}{A}\right)\right]^E$$

where t is the estimated VF duration in seconds, A, B, C, D and E are parameters and Q is the value of the quality marker.

Q may represent more than one quality marker, and in general a linear combination of the marker values may be used:

$$Q = p(AS) + q(MS) + r(DA) + s(FR)$$

where p, q, r and s are coefficients (scaling factors).

A, B, C, D, E, p, q, r and s are empirically derived from a database of ECG signals during VF known to represent a range of ECG qualities. For a particular ECG signal, a quality marker is calculated at every sample. Using the quality marker, an estimation of t is attempted and a comparison to the real time for VF duration is carried out. The values for the parameters and coefficients are iteratively adjusted with the aim of minimising the difference between the estimated VF duration and the real one.

The following are the likely ranges of the constants A, B, C, D and E:

A=+1 to +1000
B=−500 to +500
C=+1 to +500
D=0 to +200
E=+1/2 to +5/2

Defibrillator Hardware

Figure 4:
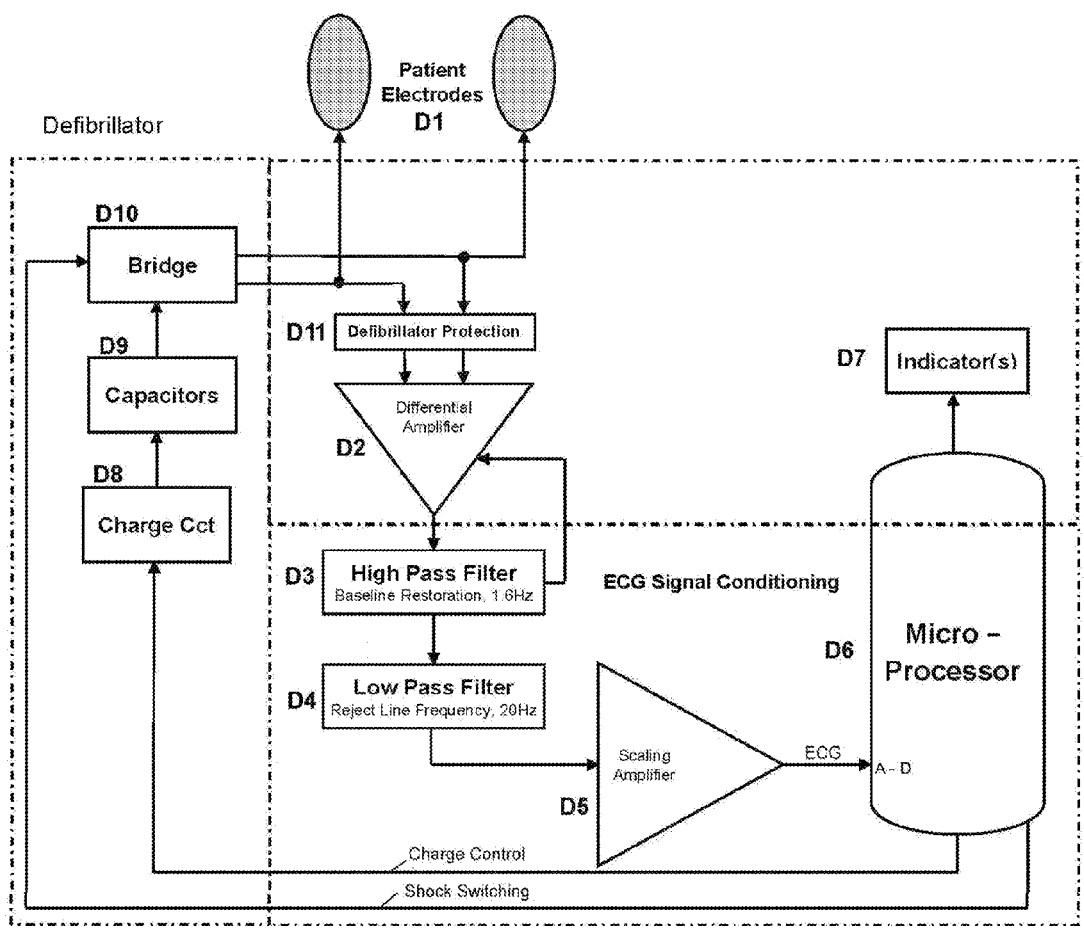
FIG. 4 is a block diagram of an automated external defibrillator embodying the invention.

FIG. 4 is a block diagram of an automated external defibrillator embodying the invention.

The hardware used in the embodiment is standard to an automated external defibrillator and involves the measurement of the ECG potentials through the two electrodes D1 which also serve to deliver the shock therapy when required.

In use, the patient's ECG is sensed by the defibrillator electrodes D1 and passed to a differential amplifier D2. The latter is protected by circuitry D11 from the high voltage which, if required by the patient, is applied to the defibrillation electrodes D1 during electro-therapy. The resultant signal (±3 mV) is passed to a first-order high pass filter D3 which, by means of feedback into the differential amplifier D2, restores the DC level to zero and removes the effects of respiration and movement (below 1.6 Hz). The resultant signal is passed to a fourth-order low pass filter D4 to remove mains pick-up and any other high frequency noise (above 20 Hz). Finally, the signal is scaled in an amplifier D5 to a level required by a microprocessor D6 for analogue-to-digital conversion and sampling. In this embodiment such sampling occurs at a rate of 170.6 samples per second.

The microprocessor D6 not only analyses the ECG signal, using known techniques, to determine whether or not the patient is in ventricular fibrillation, but controls indicators D7 which guide the user in the delivery of the electro-therapy. The indicators may comprise voice prompts and/or coloured lamps which are illuminated to indicate predetermined conditions.

On detecting VF, the microprocessor D6 automatically initiates a VF duration algorithm (to be described below) to estimate the current phase of the VF. Depending on the outcome, the defibrillator will either advise the application of CPR (to increase the quality and therefore likely effectiveness of any shock) or advise immediate shock. When a shock is advised, whether immediate or after CPR, charging of capacitors D9 will be initiated by the microprocessor D6 through activation of the charge circuit D8. The voltage on the capacitors is sensed by the microprocessor and, when at the correct energy level to be applied to the patient, a bridge D10 is activated to apply a biphasic shock to the patient when a "Shock" button (not shown) s pressed by the user.

It should be noted that the hardware shown in FIG. 4 is largely standard to all automated external defibrillators. The difference from the conventional machines is the ability to estimate the duration of the VF and to advise the user via voice prompts and/or coloured lamps D7 as to whether immediate electro-therapy or CPR followed by electro-therapy is advised. This is achieved using a novel algorithm embedded in the microprocessor software.

Defibrillator Software

The steps of the software algorithm are:

If VF is detected:

a. Determine the value Q of the quality markers, or such of them as are used, for the preceding 4-second epoch of the ECG. Thereafter, for each digital sample, update the value Q for the immediately preceding 4-second epoch of the ECG. After the initial calculation of Q the calculation is an updating process rather than a full calculation, in order to keep processing time to a minimum. This ensures both avoid CPU overload and the minimum delay in advising or administering the correct therapy. In the present embodiment only the markers AS and DA are calculated, and the value Q is given by:

$$Q = 0.75(AS) + 0.25(DA)$$

b. At certain predefined intervals, e.g. every 1 sec, for the current value of Q estimate the duration t of VF from its onset using the foregoing model. In this embodiment the following values were used in the model:
A=480
B=0
C=180
D=85
E=+1/2 c. Determine the phase of VF. VF is deemed to be in the Electrical Phase if t is lower than 240 seconds (4 min).

d. Recommend action to the user by audible and visual guidance and advice via the indicator(s) D7:

If VF is in the Electrical Phase, immediate shock therapy is recommended and the defibrillator shock circuits are enabled.

If VF is not in the Electrical Phase, CPR is recommended prior to shock therapy. The defibrillator shock circuits are not enabled until it is recommended that CPR be given, but may be manually overridden.

Figure 5:
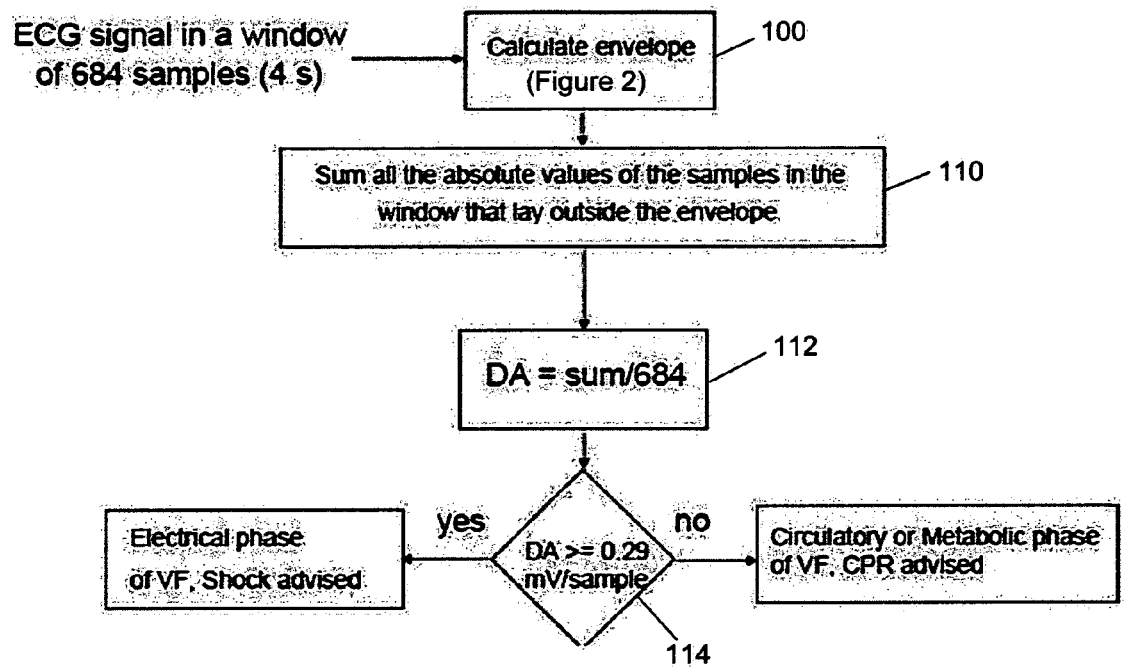
FIG. 5 is a flow diagram of a further embodiment.

FIG. 5 is an alternative algorithm for determining the VF phase in the case of the DA quality marker. As before, for each 4-second epoch the envelope 10 is calculated as described with reference to FIGS. 2 and 3, step 100. In steps 110 and 112 the DA quality marker is determined according to the formula for DA given earlier as the average of the absolute values of the samples in the epoch that lay above the envelope.

Next, however, a direct estimation of the VF phase is made by comparing the value of DA with a predetermined threshold level, step 114. In the present embodiment this threshold is 0.29 mV/sample, and if DA is equal or greater than this threshold VF is assumed to be in the Electrical Phase. Thus immediate shock therapy is recommended and the defibrillator shock circuits are enabled.

If DA is less than the threshold, it is assumed that VF is not in the Electrical Phase. Thus CPR is recommended prior to shock therapy. The defibrillator shock circuits are not enabled until it is recommended that CPR be given, but may be manually overridden.

It will be seen that this embodiment avoids the need to estimate the duration of VF.

The invention is not limited to the embodiments described herein which may be modified or varied without departing from the scope of the invention.

The invention claimed is:

1. An external defibrillator comprising:
a processor;
a pair of electrodes; and
a non-transitory computer-readable storage medium having instructions stored which, when executed by the processor, perform operations comprising:
receiving electrical signals from the pair of electrodes when the pair of electrodes are in contact with a patient;
determining, from the electrical signals, an electrocardiogram of the patient; and
when, based on the electrocardiogram, the patient is in a state of ventricular fibrillation:
identifying a density of peaks over a period of time in the electrocardiogram;
estimating a current phase of ventricular fibrillation based on the density of peaks and a median slope over the period of time; and
outputting an instruction based on the current phase.

2. The external defibrillator of claim 1, wherein estimating of the current phase of ventricular fibrillation further comprises comparing the density of peaks to an envelope.

3. The external defibrillator of claim 2, wherein the density of peaks is calculated based on a number of peaks which exceed a threshold of the envelope within the period of time.

4. The external defibrillator of claim 1, wherein the estimating of the current phase of ventricular fibrillation is further based on a frequency ratio of the ventricular fibrillation over the period of time.

5. The external defibrillator of claim 1, wherein outputting of the instruction comprises outputting an audible signal.

6. The external defibrillator of claim 5, wherein the audible signal indicates the patient is not in an electrical state of ventricular fibrillation and cardiopulmonary resuscitation should begin.

7. The external defibrillator of claim 5, wherein the audible signal indicates the patient is not in an electrical state of ventricular fibrillation and cardiopulmonary resuscitation should begin.

8. An external defibrillator comprising:
a processor;
a pair of electrodes; and
a non-transitory computer-readable storage medium having instructions stored which, when executed by the processor, perform operations comprising:
receiving electrical signals from the pair of electrodes when the pair of electrodes are in contact with a patient;
determining, from the electrical signals, an electrocardiogram of the patient; and
when, based on the electrocardiogram, the patient is in a state of ventricular fibrillation;
identifying a density of peaks over a period of time in the electrocardiogram;
estimating a current phase of ventricular fibrillation based on the density of peaks; and
outputting an instruction based on the current phase;
wherein the estimating of the current phase of ventricular fibrillation is further based on an average of slopes over the period of time and a frequency ratio of the ventricular fibrillation over the period of time.

9. An external defibrillator comprising:
a processor;
a pair of electrodes; and
a non-transitory computer-readable storage medium having instructions stored which, when executed by the processor, perform operations comprising:
receiving electrical signals from the pair of electrodes when the pair of electrodes are in contact with a patient;
determining, from the electrical signals, an electrocardiogram of the patient; and
when, based on the electrocardiogram, the patient is in a state of ventricular fibrillation;
identifying a density of peaks over a period of time in the electrocardiogram;
estimating a current phase of ventricular fibrillation based on the density of peaks; and
outputting an instruction based on the current phase;
wherein the density of peaks is calculated based on a duration of ventricular fibrillation, the duration of ventricular fibrillation being calculated using quality marker(s) is calculated as:

$$t = -B + C\left[-\ln\left(\frac{Q-D}{A}\right)\right]^E$$

where t represents a duration of the ventricular fibrillation in seconds, A, B, C, D, and E are constants, and Q represents a value of the quality marker, if only one, or a linear combination the values of the quality markers if more than one.

10. An external defibrillator comprising:

a processor;

a pair of electrodes; and a non-transitory computer-readable storage medium having instructions stored which, when executed by the processor, perform operations comprising:

receiving electrical signals from the pair of electrodes when the pair of electrodes are in contact with a patient;

determining, from the electrical signals, an electrocardiogram of the patient; and when, based on the electrocardiogram, the patient is in a state of ventricular fibrillation:

identifying a density of peaks over a period of time in the electrocardiogram, wherein the peaks are above a threshold amplitude;

identifying a frequency ratio of power in a high frequency band over power in a low frequency band within the electrocardiogram over the period of time;

estimating a current phase of ventricular fibrillation based on the density of peaks and a frequency ratio of the ventricular fibrillation; and outputting an instruction based on the current phase;

wherein the estimating of the current phase of ventricular fibrillation is further based on an average of slopes over the period of time or a median slope over the period of time.

11. An external defibrillator comprising:

a processor;

a pair of electrodes; and a non-transitory computer-readable storage medium having instructions stored which, when executed by the processor, perform operations comprising:

receiving electrical signals from the pair of electrodes when the pair of electrodes are in contact with a patient;

determining, from the electrical signals, an electrocardiogram of the patient; and when, based on the electrocardiogram, the patient is in a state of ventricular fibrillation:

identifying a density of peaks over a period of time in the electrocardiogram;

estimating a current phase of ventricular fibrillation based on the density of peaks, an average of slopes over the period of time, a median slope over the period of time, and a frequency ratio of the ventricular fibrillation; and outputting an instruction based on the current phase.

* * * * *